(12) United States Patent
Markert et al.

(10) Patent No.: US 7,259,135 B2
(45) Date of Patent: Aug. 21, 2007

(54) USE OF HEXENAL DERIVATIVES AS PERFUMES

(75) Inventors: Thomas Markert, Monheim (DE); Marc Speitkamp, Duesseldorf (DE); Frank Rittler, Duesseldorf (DE)

(73) Assignee: Kao Corporation, Tokyo (JP)

( * ) Notice: Subject to any disclaimer, the term of this patent is extended or adjusted under 35 U.S.C. 154(b) by 169 days.

(21) Appl. No.: 10/503,588

(22) PCT Filed: Feb. 10, 2003

(86) PCT No.: PCT/EP03/01273

§ 371 (c)(1), (2), (4) Date: Aug. 12, 2004

(87) PCT Pub. No.: WO03/070864

PCT Pub. Date: Aug. 28, 2003

(65) Prior Publication Data

US 2005/0130875 A1    Jun. 16, 2005

(30) Foreign Application Priority Data

Feb. 19, 2002 (DE) ................................ 102 06 771

(51) Int. Cl.
*A61Q 13/00* (2006.01)
*A61K 8/18* (2006.01)
(52) U.S. Cl. ...................................... 512/27
(58) Field of Classification Search .................. 512/25, 512/26, 27
See application file for complete search history.

(56) References Cited

U.S. PATENT DOCUMENTS

| 3,704,714 A | 12/1972 | Kallianos et al. |
| 4,010,207 A | 3/1977 | Hall et al. |
| 4,430,233 A * | 2/1984 | Boden et al. ............... 510/101 |

FOREIGN PATENT DOCUMENTS

| FR | 1 409 326 | 8/1965 |
| FR | 2 430 402 | 2/1980 |

OTHER PUBLICATIONS

Ansell, M. F. et al. "The synthesis and reactions of branched-chain hydrocarbons. Part X. The rearrangement of alpha-ethynyl alcohols to unsaturated carbonyl compounds", Journal of the Chemical Society. pp. 911-917, XP002242815 1956.

* cited by examiner

*Primary Examiner*—Jill Warden
*Assistant Examiner*—Keri A Moss
(74) *Attorney, Agent, or Firm*—Oblon, Spivak, McClelland, Maier & Neustadt, P.C.

(57) ABSTRACT

The invention relates to hexenal derivatives of general structure (I), in which one of the bonds represented by dashes is a C—C single bond and the other is a C═C double bond, with the proviso that the C═C double bond can have a Z or E configuration, provided that it is in the $C^{3/4}$ position. Said derivatives are characterised by an interesting and original perfume that pervades a wide area and are suitable for use as perfumes, for example in cosmetic preparations, technical products or the alcohol-based perfume industry.

15 Claims, No Drawings

USE OF HEXENAL DERIVATIVES AS PERFUMES

FIELD OF THE INVENTION

The present invention relates to hexenal derivatives of a specific structure as perfumes.

PRIOR ART

Many natural fragrances, relative to their demand, are available in completely insufficient quantities. For example, 5,000 kg of rose petals are needed to produce 1 kg of rose oil. The consequences include a greatly limited annual production worldwide and a high price. It is therefore apparent that the fragrance industry has a constant need for new fragrances that exhibit interesting scents. On the one hand, the range of naturally available fragrances can be supplemented thereby, on the other hand it is thus possible to make the necessary adaptations to the ever-changing fashion in taste. Furthermore, this makes it possible in this manner to meet the ever-increasing demand for scent enhancers for products of daily use, such as cosmetics and cleaning agents.

Moreover, there is generally a constant demand for synthetic fragrances that can be produced inexpensively and with a uniform high quality, and which have the original olfactory characteristics. In particular, they are intended to exhibit pleasant, sufficiently intense scent profiles that are as natural as possible and are novel in terms of their quality. Such synthetic fragrances are also intended to be capable of beneficially influencing the scent of cosmetics and goods of daily use. In other words, there is a constant demand for compounds that exhibit characteristic novel scent profiles while simultaneously ensuring considerable staying power, intensity of scent and strong diffusion.

M. F. Ansell, J. W. Hancock and W. J. Hickinbottom, J. Chem. Soc. 1956, page 911, report that, in addition to the isomeric ketones during the Rupe rearrangement of 3-isobutyl-5-methyl-hex-1-in-3-ol, they obtained 5-methyl-3-isobutyl-2(3)-hexenal in small quantities. Nothing is disclosed concerning fragrant characteristics or the suitability of the compounds as fragrances.

DESCRIPTION OF THE INVENTION

It was found that the compounds of general formula (I) superlatively meet the aforementioned requirements in every way and that they can be advantageously used as fragrances exhibiting diverse nuanced scents that in turn offer good staying power.

The subject matter of the present invention is, initially, the use of hexenal derivatives of general structure (I)

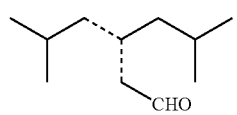

(I)

in which one of the bonds represented by dashes is a C—C single bond and the other is a C=C double bond, with the proviso that the C=C double bond can have a Z or E configuration, provided that it is in the C¾ position, said derivatives being used as fragrances.

Overall, formula (I) includes three chemical individuals, namely 5-methyl-3-isobutyl-2-hexenal (I-a)
5-methyl-3-isobutyl-3-hexenal with E-configured C=C double bond (I-b)
5-methyl-3-isobutyl-3-hexenal with Z-configured C=C double bond (I-c)

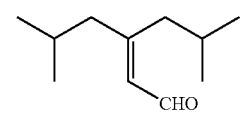

(I-a)

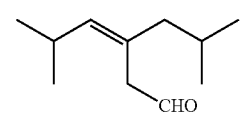

(I-b)

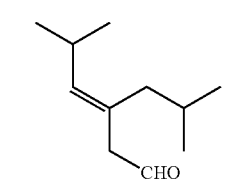

(I-c)

In the use according to the invention, compounds (I-a), (I-b) and (I-c) are employed individually or blended together. A particularly preferred use is that of blends of compounds (I-a), (I-b) and (I-c).

In a further embodiment, the invention relates to fragrance concentrates comprising one or more of the compounds of general structure (I) described above in detail.

Compounds (I) according to the invention are characterized by an odour characteristic in which citrus scents dominate. They have excellent stability in formulations for cosmetics and fragrances of daily use.

Compounds (I) may be produced on the basis of synthesizing techniques known in organic chemistry. One such process that offers convenient preparation for the production of a blend of compounds (I-a), (I-b) and (I-c) can be gathered from the section dealing with the examples.

In perfume compositions, compounds (I) enhance harmony and diffusion as well as naturalness and staying power. Dosage is tailored to whichever scent is being striven for, while taking the composition's other constituents into account.

It was not foreseeable that compounds (I) would exhibit the aforementioned scents, which provides further confirmation of the general experience that the olfactory characteristics of known fragrances do not permit automatic conclusions regarding the properties of structurally related compounds, since neither the mechanism of scent perception nor the effect of the chemical structure on scent perception have been adequately researched and since it therefore cannot normally be predicted as to whether a modified structure of known fragrances actually causes the olfactory characteristics to be modified or as to whether these modifications are assessed positively or negatively by the person skilled in the art.

Owing to their scent profile, formula (I) compounds are, furthermore, particularly suitable for modifying and enhancing known compositions. Particular emphasis should be placed on their outstanding intensity of scent, which contributes, in a quite general way, toward the composition's refinement.

Formula (I) compounds can be combined using numerous known fragrance ingredients, such as other fragrances of a natural, synthetic or partially synthetic origin, essential oils and plant extracts. The range of natural fragrances may include components that are both readily volatile as well as ones that exhibit medium and low volatility. The range of synthetic fragrances may include representatives of virtually any substance class.

Examples of suitable substances with which compounds (I) can be combined include in particular:

(a) Natural products such as evernia furfuraceae (tree moss) absolute, basilicum oil, citrus oils such as bergamot oil, mandarin oil, etc., mastic absolute, myrtle oil, palmarosa oil, patchouli oil, petit grain oil, absinth oil, myrrh oil, olibanum oil, cedar wood oil, sandal wood oil, East Indian, guajak wood oil, cabreuva, (b) Alcohols such as farnesol, geraniol, citronellol, linalool, nerol, phenylethyl alcohol, rhodinol, cinnamyl alcohol, Sandalore [3-methyl-5-(2.2.3-trimethylcyclopent-3-en-1-yl)pentan-2-ol], Sandela [3-isocamphyl-(5)-cyclohexanol], Muguetanol, (c) Aldehydes such as citral, Helional®, alpha-hexylcinnamaldehyde, hydroxycitronellal, Lilial® [p-tert.-butyl-α-methyldihydrocinnamaldehyde], methylnonylacetaldehyde, (d) Ketones such as allyl ionone, α-ionone, β-ionone, Isoraldein, methyl ionone, noot katone, Calone, α, β- and γ-Irone, Damascone, (e) Esters such as allyl phenoxyacetate, benzylsalicylate, cinnamylpropionate, citronellyll acetate, decylacetate, dimethylbenzylcarbinylacetate, ethylacetoacetate, hexenylisobutyrate, linalylacetate, methyldihydrojasmonate, vetiverylacetate, cyclohexylsalicylate, isobomylisobutyrate, Evernyl, (f) Lactones such as gamma-undecalactone, 1-oxaspiro[4.4]nonan-2-one, cylopentadecanolide, ethylene brassylate, (g) Ethers such as Herbavert, Ambroxan, as well as various further components often used in the perfume industry such as musk and sandal wood fragrances, indole, p-menthane-8-thiol-3-one, methyleugenol and methylanthranilate.

Noteworthy is, furthermore, how the structure (I) compounds round off the scents of a wide range of known compositions and harmonize these without, however, being dominant in an unpleasant manner.

The usable proportions of compounds (I) according to the invention, or blends thereof, in fragrance compositions range from approximately 1-70% by weight, based on the entire mixture. Blends of compounds (I) according to the invention as well as compositions of this type can be used both to perfume cosmetic preparations, such as lotions, creams, shampoos, soaps, ointments, powders, aerosols, toothpastes, mouthwash and deodorants as well as in alcoholic perfumery (e.g. eau de cologne, eau de toilette, extracts). There is also the possibility to use the aforementioned to perfume technical products such as detergents and cleaning agents, fabric softeners and textile treating agents. To perfume these various products, the compositions are added thereto in an amount effective olfactorily, in particular in a concentration of 0.01 to 2% by weight, based on the entire product. These values do not, however, constitute limits since the experienced perfumer can still attain effects with even lesser concentrations or can construct novel complexes with even higher dosages.

EXAMPLES

Example 1

Production of 4,4-diethoxy-2,6-dimethyl-heptane

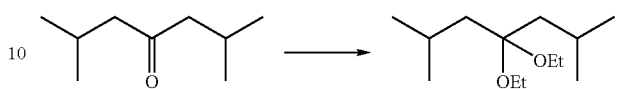

Charge:
1) 710.6 g (4 mol) 2,6-dimethyl-4-heptanone
2) 710.0 g (4.8 mol) triethyl orthoformate
3) 1.3 g (13.3 mmol) sulphuric acid, concentrated
4) 900 g ethanol, MEK denatured 99%

Apparatus: 4-litre 3-necked flask, agitator, thermometer, nitrogen atmosphere

Execution: components 1), 2), 4) and 3) were added, one after the other, to the reaction flask and stirred for 7 hours at room temperature in a nitrogen atmosphere. The course of the reaction was monitored by means of gas chromatography (GC). After 7 hours, 43% of the product had formed. 3.6 g sodium methanolate solution (30% in methanol) was then added for the purpose of neutralization. Excess ethanol and the ethyl formate obtained were removed by distillation in a rotation evaporator in a water jet vacuum. 730 g crude diethylketal of the 2,6-dimethyl-4-heptanone was distilled in a 20-cm Vigreux column. 227 g of main product (boiling point: 48° C./0.09 mbar) with a GC purity of 98.4% was used for the further reaction.

Example 2

Production of 4-(2,2,-diethoxy-ethyl)-2,6-dimethyl-4-ethoxy-heptane

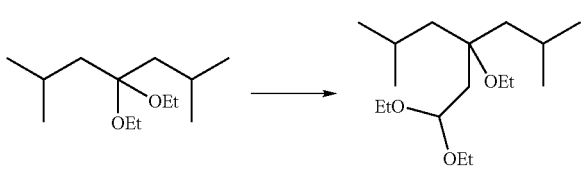

Charge:
1) 360.2 g (1.6 mol) 4,4-diethoxy-2,6-dimethyl-heptane (produced according to example 1)
2) 160 ml zinc chloride solution (10% in ethyl acetate)
3) 138.2 g (1.92 mol) ethyl vinyl ether Apparatus: 2-litre agitator with thermometer, reflux cooler and drip funnel Execution: components 1) and 2) were weighed out, one after the other, into the reaction flask and were heated to 42° C. while being stirred. Component 3) was continuously fed thereto for 1.5 hours while being stirred. It was stirred for another 8 hours at 40° C. No complete conversion took place, however. 1.4% of the starting material did not react.

Under the reaction conditions, 37% of the diethylketal had eliminated ethanol and had formed the enol ether that no longer continued to react.

Further processing: the charge was transferred to a separating funnel and washed neutral with water and sodium hydrogencarbonate solution. The organic phase was dried over sodium sulphate and concentrated on a rotation evaporator.

376.3 g of crude product having a product content of 35% (2 isomers) was obtained. This was distilled in a Vigreux column. In the main run, 112.3 g of 4-(2,2-diethoxy-ethyl)-2,6-dimethyl-4-ethoxy-heptane (boiling point 73-84° C./0.08 mbar, GC purity 98.7%) (2 isomers) was obtained.

Analysis: the IR spectrum (film between NaCl) showed characteristic ether bands at 996, 1069, 1124 and 1157 cm$^{-1}$.

The $^1$H-NMR spectrum (400 MHz in CDCl$_3$) showed 4 methyl groups as doublets at 1.2 ppm and 3 methyl groups as triplets at 0.8 and 0.9 ppm. The 2 CH$_2$ groups yielded signals between 1.6 and 2.0 ppm as multiplets of doublets. 3 CH$_2$ groups of ethyl radicals yielded quadruplets at 3.3, 3.5 and 3.6 ppm. A single proton was found at 4.7 ppm (triplet, acetal proton), accompanied by a less intensive triplet for one isomer. The two remaining protons at C-2 and C-6 are presumed at 1.3-1.5 ppm, though they were not discernible as nonets.

Scent characteristic: when first smelled, it was slightly fruity, evoking berries, petroleum, green, chocolate; after 24 hours on the scent strip, the scent was faintly redolent of cumin, with lardaceous, woody hints.

Example 3

Representation of 5-methyl-3-osobutyl-3-hexenal blended with 5-methyl-3-isobutyl-3-hexenal

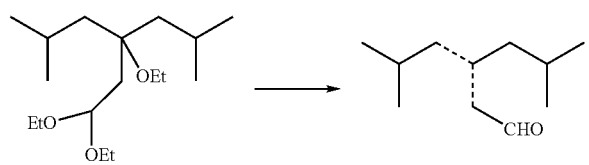

Charge:
1) 111.1 g (0.39 mol) 4-(2,2-diethoxy-ethyl)-2,6-dimethyl-4-ethoxy-heptane (produced according to example 2)
2) 67.3 g (1.46 mol) formic acid
3) 17.9 g (0.26 mol) sodium formate
4) 28.6 g water Apparatus: 0.5-litre agitator with thermometer, reflux cooler and drip funnel Execution:

Components 2), 3) and 4) were charged and heated to the reflux temperature (94° C.) while being stirred. The acetal produced according to example 2—component 1)—was added dropwise continuously for 1 hour. The reflux temperature dropped to 80° C. during this procedure. It was refluxed (78-62° C.) for another 5 hours. The same quantity of components 2), 3) and 4) was then added once more and refluxed for another 5 hours.

The reaction mixture was cooled, transferred to a separating funnel and the aqueous phase was separated. The organic phase was washed with 500 ml iced water. The aqueous phase was extracted 3 times with ether. The organic phases were combined and washed 1× with water, 2× with sodium hydrogencarbonate solution, 2× with soda solution and 1× with water. They were then dried over MgSO$_4$ and concentrated on a rotation evaporator. 48.3 g crude product was obtained.

The crude product's distillation in a 20-cm Vigreux column yielded 32 g main product (boiling point 54-55° C./0.06 mbar); purity, as determined by gas chromatography, was 99%.

The IR spectrum (film between NaCl) showed carbonyl vibrational bands at 1676 and 1724 cm$^{-1}$ and 2 bands at 2765 cm$^{-1}$.

The $^1$H-NMR spectrum (400 MHz in CDCl$_3$) was very complex and is interpreted as follows: the 12 protons of the 4 methyl groups are all between 0.8 and 1.0 ppm. Several signals and groups that are to an extent split up into strong signal clusters vary between 1.1 and 2.5 ppm, so that they cannot be assigned clearly. 3 doublets are visible as an olefinic proton between 5.8 and 6.0 ppm, coupled with approx. 4 doublets for the aldehyde proton at 9.9 and 10.0 ppm.

Scent characteristic: when first smelled, it was lardaceous, fruity, citrus, citral; after 24 hours on the scent strip, the subsequent smell was rancid, lardaceous, redolent of paint, sweat, petroleum.

The invention claimed is:

1. A method of fragrancing a product comprising applying a composition comprising a hexenal derivatives of general structure (I)

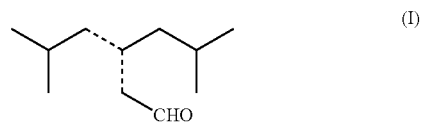

in which one of the bonds represented by dashes is a C—C single bond and the other is a C═C double bond, with the proviso that said C═C double bond can have a Z or E configuration, provided that it is in the C¾ position, to a product.

2. A fragrance composition having a content of one or more compounds (I) of general structure (I)

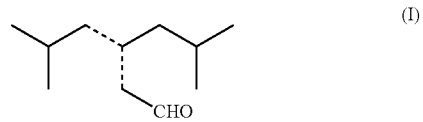

in which one of the bonds represented by dashes is a C—C single bond and the other is a C═C double bond, with the proviso that said C═C double bond can have a Z or E configuration, provided that it is in the C¾ position, said compounds (I) being present in an amount of 1 to 70% by weight, based on the entire composition.

3. The method of claim 1, wherein said composition is applied in an amount of 0.01 to 2 wt. % based on the entire product.

4. The method of claim 1, wherein said product is a cosmetic preparation.

5. The method of claim 4, wherein said cosmetic preparation is selected from the group consisting of a lotion, a cream, a shampoo, a soap, an ointment, a powder, an aerosol, a toothpaste, a mouthwash, a deodorant and an alcoholic perfumery.

6. The method of claim 1, wherein said product is selected from the group consisting of a detergent, a cleaning agent, a fabric softener and a textile treating agent.

7. The method of claim 1, wherein said hexenal derivative is 5-methyl-3-isobutyl-2-hexenal.

8. The method of claim 1, wherein said hexenal derivative is 5-methyl-3-isobutyl-3-hexenal with an E-configured C=C double bond.

9. The method of claim 1, wherein said hexenal derivative is 5-methyl-3-isobutyl-3-hexenal with a Z-configured C=C double bond.

10. The method of claim 1, wherein said composition further comprises a fragrance ingredient.

11. The method of claim 10, wherein said fragrance ingredient is at least one selected from the group consisting of evernia furfuraceae (tree moss) absolute, basilicum oil, bergamot oil, mandarin oil, mastic absolute, myrtle oil, palmarosa oil, patchouli oil, petit grain oil, absinth oil, myrrh oil, olibanum oil, cedar wood oil, sandal wood oil, East Indian, guajak wood oil, cabreuva, farnesol, geraniol, citronellol, linalool, nerol, phenylethyl alcohol, rhodinol, cinnamyl alcohol, Sandalore [3-methyl-5-(2.2.3-trimethyl-cyclopent-3-en-1-yl)pentan-2-ol], Sandela [3-isocamphyl-(5)-cyclohexanol], Muguetanol, citral, Helional®, alpha-hexylcinnamaldehyde, hydroxycitronellal, Lilial®[p-tert-butyl-α-methyldihydrocinnamaldehyde], methylnonylacetaldehyde, allyl ionone, α-ionone, β-ionone, Isoraldein, methyl ionone, noot katone, Calone, α-Irone, β-Irone, γ-Irone, Damascone, allyl phenoxyacetate, benzylsalicylate, cinnamylpropionate, citronellyll acetate, decylacetate, dimethylbenzylcarbinylacetate, ethylacetoacetate, hexenylisobutyrate, linalylacetate, methyldihydrojasmonate, vetiverylacetate, cyclohexylsalicylate, isobornylisobutyrate, Evernyl, gamma-undecalactone, 1-oxaspiro[4.4]nonan-2-one, cylopentadecanolide, ethylene brassylate, Herbavert, Ambroxan, musk fragrance, sandal wood fragrance, indole, p-menthane-8-thiol-3-one, methyleugenol, methylanthranilate and a mixture thereof.

12. The fragrance concentrate of claim 2, wherein said hexenal derivative is 5-methyl-3-isobutyl-2-hexenal.

13. The fragrance concentrate of claim 2, wherein said hexenal derivative is 5-methyl-3-isobutyl-3-hexenal with an E-configured C=C double bond.

14. The fragrance concentrate of claim 2, wherein said hexenal derivative is 5-methyl-3-isobutyl-3-hexenal with a Z-configured C=C double bond.

15. The fragrance concentrate of claim 2, further comprising a fragrance ingredient.

* * * * *